United States Patent [19]

Coates

[11] Patent Number: 5,412,320
[45] Date of Patent: May 2, 1995

[54] NUCLEAR MAGNETIC RESONANCE DETERMINATION OF PETROPHYSICAL PROPERTIES OF GEOLOGIC STRUCTURES

[75] Inventor: George R. Coates, Austin, Tex.
[73] Assignee: Numar Corporation, Malvern, Pa.
[21] Appl. No.: 898,990
[22] Filed: Jun. 15, 1992

Related U.S. Application Data

[63] Continuation-in-part of Ser. No. 701,516, May 16, 1991, abandoned.

[51] Int. Cl.$^6$ .............................................. G01V 3/00
[52] U.S. Cl. ...................................... 324/303; 324/307
[58] Field of Search .................. 324/303, 300, 307, 309

[56] References Cited

U.S. PATENT DOCUMENTS

| 4,710,713 | 12/1987 | Taicher et al. | 324/303 |
|---|---|---|---|
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,933,638 | 6/1990 | Kenyon et al. | 324/303 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |

OTHER PUBLICATIONS

Miller, M., et al; "Spin Echo Magnetic Resonance Logging; Porosity and Free Fluid Determination", SPE20516, Oct. 1990.
Coates G., et al.; "The MRIL in Conoco 33-1, An Investigation of a new Magnetic Resonance Imaging Log", 1991 SPWLA Trans. (month unknown).
Coates, G., et al.; "The Magnetic Resonance Imaging Log Characterized with Petrophysical Properties and Laboratory Core Data", SPE22723, Oct. 1991.
Worthington, P. F., "The Evolution of Shaly Sand Concepts in Reservoir Evaluation", The Log Analyst, Jan.–Feb. 1985.
Coates, G., et al.; "A New Approach to Improved Log Derived Permeability", 1973 SPWLA Trans.
Archie, G., "The electrical resistivity as an aid in determining some reservoir characteristics", 1942 AIMM Engineers Trans.
Clavier, C., et al.; "The Theoretical and Experimental Bases for the Dual Water Model for the Interpretation of Shaly Sands", Journal of Petroleum Technology, Apr. 1984.
Dumanoir, J., et al., "$R_{xo}/R_t$ Methods for Wellsite Interpretation," The Log Analysts, vol. XIII, 1972.
Timur, A., "An Investigation of Permeability, Porosity, and Residual Water Saturation Relationship", 1968 SPWLA Transactions.

Primary Examiner—Louis Arana
Attorney, Agent, or Firm—Pennie & Edmonds

[57] ABSTRACT

An improved system for using magnetic resonance techniques to obtain information relating to geologic structures. The system of the present invention uses values of bulk-volume irreducible water and porosity obtained via the magnetic resonance techniques to obtain additional information relating to geologic structures, including water saturation.

20 Claims, 15 Drawing Sheets

NUCLEAR MAGNETIC RESONANCE DETERMINATION OF PETROPHYSICAL PROPERTIES OF GEOLOGIC STRUCTURES

CONTINUING APPLICATION DATA

This application is continuation-in-part of application Ser. No. 07/701,516, filed May 16, 1991, abandoned.

FIELD OF INVENTION

The present invention relates to systems for obtaining quantitative and qualitative measurements of geologic structures. More specifically, the present invention provides an efficient and effective method for using information obtained via nuclear magnetic resonance techniques to determine petrophysical properties of geologic structures.

BACKGROUND

As is known, a key petrophysical property in determining whether a formation will produce viable amounts of hydrocarbons is the water saturation, $S_w$, of the formation. $S_w$ is defined as the percentage pore space of the formation that is filled with formation water. If a formation's porosity (PHI) is completely filled with water, $S_w = 100\%$. Obviously, such a formation is of no interest to a person searching for oil. $S_w$ is related to the bulk-volume water (BVW) of the formation, i.e., the percentage of the unit volume of the formation that is formation water, as follows:

$$BVW = PHI * S_w.$$

The minimum possible water saturation of a formation is known as irreducible water saturation, $S_{WIRR}$. A zone that is at irreducible water saturation will produce all hydrocarbons and no water. The irreducible water saturation of a formation is related to the average grain size of a formation. For example, shales and clays, due to their platy structure and small grain size have immense surface areas compared to the same volume of sand grains. The effect of this is to bind large quantities of water to their structure. Additionally, due to their fine grain size and the strong forces that hold the water in place, shales have essentially zero permeability and high porosity. Thus, shales decrease the porosity of the formation that is available to hold free fluids and increase the amount of water that is bound to the formation. $S_{WIRR}$ is related to the water bound to the formation, known as the bulk-volume irreducible water (BVI) of the formation, i.e., the percentage of the unit volume of the formation that is irreducible formation water, as follows:

$$BVI = PHI * S_{WIRR}.$$

Given the critical importance of the $S_w$ as discussed above, many techniques have been proposed for determining its value for a given formation. In log interpretation, the standard approach to water saturation is through the Archie formation factor process. The formation factor F is defined as follows:

$$F = R_o/R_w = C_w/C_o$$

where $R_o$ is the resistivity of a reservoir rock when fully saturated with aqueous electrolyte of resistivity $R_w$, and $C_o$ and $C_w$ are corresponding conductivities. Further, given knowledge of porosity (PHI) and resistivity ($R_t$), i.e., the resistance of reservoir rock that is partially saturated to degree $S_w$ with electrolyte of resistance $R_o$, via conventional logging techniques, Archie formation factor analysis provides the necessary empirical relationships to relate porosity (PHI) to formation factor (F) and resistivity to saturation. The relationships are:

$$F = \frac{a}{PHI^m}$$

and $$S_w^n = \frac{FR_w}{R_t}$$

In practice, the values of "a" (formation-factor coefficient), "m" (cementation exponent), and "n" (saturation exponent) vary with the type of formation and the nature of the hydrocarbon. However, in most cases an analyst will use the same relationship over large intervals, intervals that may include a variety of lithologies, pore types, and grain sizes. In such circumstances, it is often difficult to select the correct values of "a", "m", and "n". A selection of the correct values is of a significant concern since these parameters are used to relate porosity to formation factor F, and, in conjunction with resistivity, to saturation.

In an attempt to reduce the complexity of the above-mentioned relationships, it is has been observed that if "a" is a constant, it should equal to 1, since F must be equal to 1.0 in 100% porosity. Thus, the relationship between formation factor F and porosity reduces to:

$$F = \frac{1}{PHI^m}$$

With respect to the exponential relationships "m" and "n" used in this process, as log analysts know, these describe a link between resistivity and saturation as if the response was independently linked to porosity and saturation. While this model has been useful for performing laboratory studies of geologic structures, the complexity of the model is not necessary for interpreting an actual resistivity log. To a resistivity or conductivity log, the controlling factors are the volume of fluids and their conductivity.

Considering the above, a slightly different approach has been proposed. The proposed approach eliminates porosity and saturation as independent variables and uses only the bulk-volume water term (the product of porosity and saturation) to model the relationship between the conductivity of the fluids involved and the measured conductivity of the formation.

In an article by George R. Coates and J. L. Dumanoir, entitled "A New Approach to Improved Log-Derived Permeability," SPWLA, Fourteenth Annual Logging Symposium, p.1, 1973, it was found that a common value, "w", could be adopted for both the saturation exponent, "n", and cementation exponent, "m". The proposed single exponent expression used to relate BVW, i.e., $PHI*S_w$, to resistivity is:

$$(PHI*S_w)^w = R_w/R_t$$

where:
w is the single exponent used to relate the BVW to $R_w/R_t$;

PHI is the total porosity of the rock;
$R_w$ is the resistivity of the formation water; and
$R_t$ is the true resistivity of the rock.

The proposed single exponent expression discussed above has not been widely used in the logging industry up to now because previously, a log analyst could only assume a rock to be water filled in order to examine an apparent value for w. In other words, the single exponent equation could only be solved for w by assuming that PHI*$S_w$=PHI, since porosity was determinable via conventional logging instruments.

The results obtained by assuming a water filled condition were only valid in the water zones and resulted in an overestimation of w in the hydrocarbon zones of interest. It has long been desired to solve w for a hydrocarbon filled condition, i.e., PHI*$S_w$=BVI, such that a valid result for w could be obtained for hydrocarbon zones of interest.

With the advent of nuclear magnetic resonance (NMR) logging, new options for determining w as well as other fluid flow properties of porous media have arisen. In an article by A. Timur, entitled "Pulsed Nuclear Magnetic Resonance Studies of Porosity, Movable Fluid, and Permeability of Sandstones," in the Journal of Petroleum Technology, June 1969, page 775, it was shown experimentally that NMR methods provide a rapid non-destructive determination of porosity, movable fluid, and permeability of rock formation.

It is known that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter T1, known as the spin-lattice relaxation time.

It has been observed that the mechanism which determines the value of T1 depends on molecular dynamics. In liquids, molecular dynamics are a function of molecular size and inter-molecular interactions. Therefore, water and different types of oil have different T1 values.

In the heterogeneous media, such as a porous solid which contains liquid in its pores, the dynamics of the molecules close to the solid surface are also significant and differ from the dynamics of the bulk liquid. It may thus be appreciated that the T1 parameter provides valuable information relating to well logging parameters.

There exist a number of techniques for disturbing the equilibrium of an assembly of magnetic moments, such as those of hydrogen nuclei, for T1 parameter measurements. Each of these techniques provides means for measuring T1 of a rock formation within a certain volume (called the "sensitive volume") which is determined mainly by the shape of the magnetic field surrounding the magnetic structure. The signal-to-noise ratio of the measurement is limited by the ratio of the sensitive volume to the uniformity of the magnetic field within said volume (maximum flux density minus minimum flux density), and increases in proportion to this ratio.

In any given nuclear magnetic resonance instrument configuration, the apparatus will respond only to nuclei residing within the sensitive volume. In the present invention and prior art instruments described herein, the boundaries of the sensitive volume are determined by radiation patterns of transmitting and receiving antennae as well as a combination of the detailed structure of the magnetic field with the receiver's frequency passband. The radio frequency that a given nucleus will respond to or emit when excited is proportional to the flux density of the magnetic field in which it is immersed. The proportionality factor depends upon the nuclear species. For hydrogen nuclei, that factor is 42.5759 MHz/Tesla. If the NMR receiver's passband extends from 1.30 MHz to 1.31 MHz, the instrument will be sensitive to hydrogen nuclei in regions of the magnetic field that have flux densities between 30.5 mT and 30.8 mT, providing the antenna radiation pattern allows receiving sufficient signal from that locations.

If it is desired to study nuclei located within a particular region, the magnetic field structure, antenna radiation pattern and receiver passband must all be adjusted to be sensitive to that and only that region. Since the signal-to-noise ratio of the resulting signal is proportional to (among other factors) the square root of the receiver passband width, it is important to minimize the variation of the magnetic field within the desired sensitive volume; smaller variations (better field uniformity) mean a better signal-to-noise ratio. Since the signal-to-noise ratio also increases with increasing frequency, the nominal magnetic field intensity within the volume is also very important. It is immaterial whether this nominal intensity is defined as the central value, average value or some other value within the range of values encompassed by the sensitive volume because only large differences in signal-to-noise ratio are significant.

One technique for measuring T1 of a rock formation is exemplified by what is known as the "Schlumberger Nuclear Magnetic Logging Tool." That tool is described by R. C. Herrick, S. H. Couturie, and D. L. Best in "An Improved Nuclear Magnetic Logging System and Its Application to Formation Evaluation," SPE8361 presented at the 54th Annual Fall Technical Conference and Exhibition of the Society of Petroleum Engineers of AIME, held in Las Vegas, Nev., Sep. 23–26, 1979, and also by R. J. S. Brown et al. in U.S. Pat. No. 3,213,357 entitled "Earth Formation and Fluid Material Investigation by Nuclear Magnetic Relaxation Rate Determination."

The Schlumberger Nuclear Magnetic Logging Tool measures the free precession of proton nuclear magnetic moments in the earth's magnetic field by applying a relatively strong DC polarizing field to the surrounding rock formation in order to align proton spins approximately perpendicularly to the earth's magnetic field. The polarizing field must be applied for a period roughly five times T1 (the spin-lattice relaxation time) for sufficient polarization (approximately two seconds). At the end of polarization, the field is turned off rapidly. Since the protons spins are unable to follow this sudden change, they are left aligned perpendicularly to the earth's magnetic field and precess about this field at the "Larmor Frequency" corresponding to the local earth's magnetic field (roughly from 1300 to 2600 Hz, depending on location).

The spin precession induces in a pick-up coil a sinusoidal signal whose amplitude is proportional to the density of protons present in the formation. The signal decays with a time contrast "T2" (transverse relaxation time) due to non-homogeneities in the local magnetic field over the sensing volume.

Improved nuclear magnetic resonance logging tools and methods for using these tools are described generally in U.S. Pat. Nos. 4,710,713; 4,717,876; 4,717,877;

and 4,717,878, all of which are commonly owned by the assignee of the present invention.

The method of the present invention, described in greater detail below, uses the logging tool and techniques described in the above referenced patents to obtain previously unavailable data relating to the composition of a geologic structure. Additionally, the primary measurements of the above described tools are used in combination with new and existing theories to obtain enhanced information regarding petrophysical properties of geologic structures. In particular, newly available data is linked to a key petrophysical property, water saturation.

SUMMARY OF THE INVENTION

The method of the present invention provides an improved system for using nuclear magnetic resonance techniques for obtaining information relating to geologic structures. In the system of the present invention, a nuclear magnetic resonance logging tool is used to impart magnetic polarization fields on a portion of a geologic formation. Nuclear magnetic resonance signals from the excited nuclei in the formation are then detected to obtain data for calculating a number of important petrophysical parameters including the porosity and the bulk volume irreducible water of the formation.

The availability of a direct measure of the volume of irreducible water (BVI), as provided by the above-mentioned devices, is used to improve the reliability of log derived water saturations, especially in complex lithologies.

In a preferred embodiment, the porosity and the bound volume irreducible water are further used to determine additional petrophysical properties of the formation, including bulk volume water. In particular, the bulk volume water is calculated by solving the expression:

$$(PHI^*S_w)^w = R_w/R_t$$

for a first apparent w by assuming a water filled formation (PHI*S$_w$=PHI) and for a second apparent w by assuming an oil filed formation (PHI*S$_w$=BVI).

Additional petrophysical parameters are derived from the apparent values of w including a quick look irreducible saturation profile based on the interplay between a modeled relationship for w and the two apparent values of w.

DETAILED DESCRIPTION OF THE PREFERRED EMBODIMENT

Figure 1:
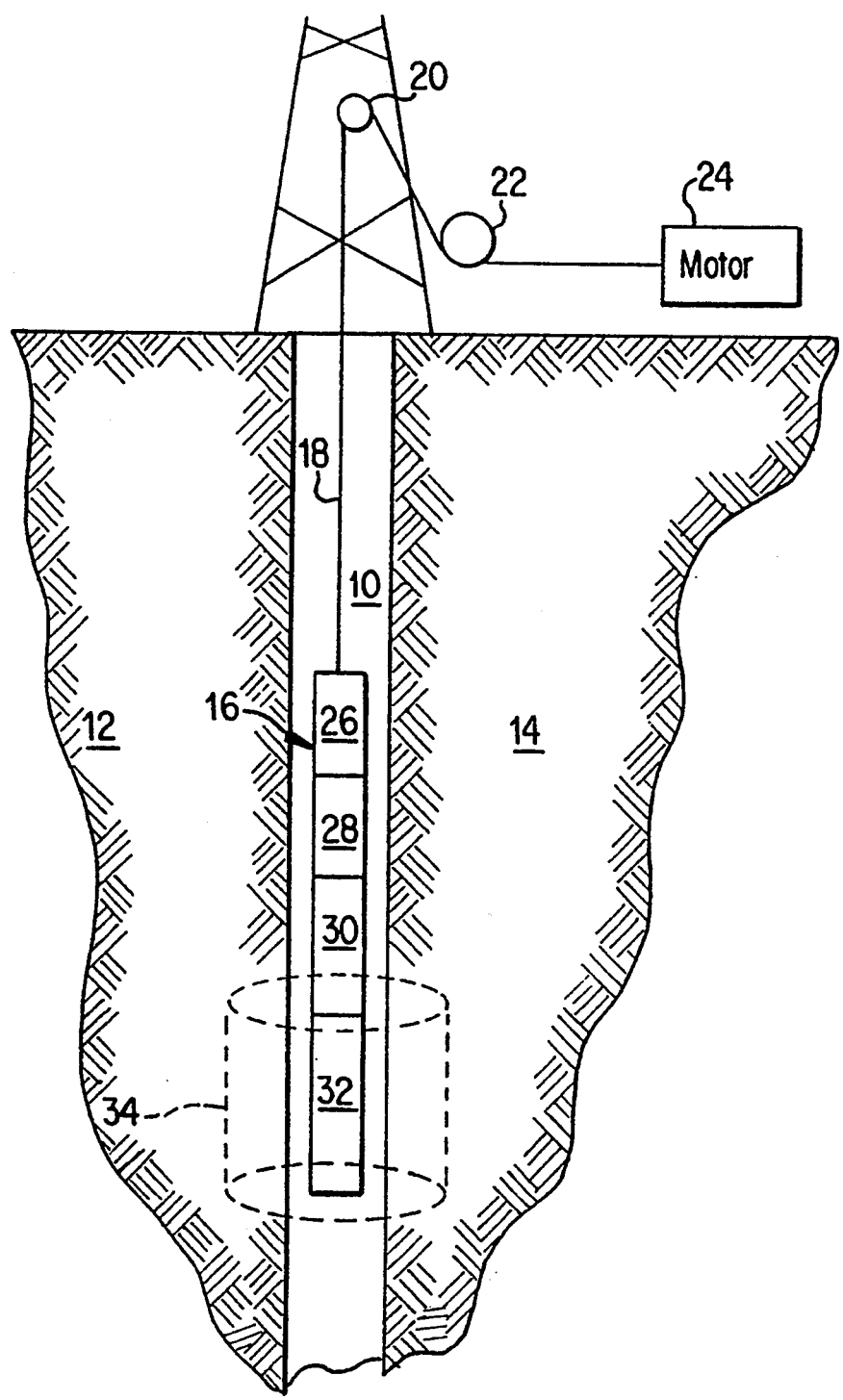
FIG. 1 is a partially pictorial, partially block diagram illustration of a well logging apparatus for obtaining nuclear magnetic resonance measurements of a geologic structure.

Referring to FIG. 1, a borehole 10 is shown in formation 12 having structures to be examined using the method and apparatus of the present invention. Within the borehole, there is a logging tool 16 which is suspended by a cable 18 routed over pulleys 20 and 22, with the position of the cable 18 being determined by a motor 24.

The upper portion of the logging tool 16 comprises telemetry electronics 26, gamma ray sensing electronics 28 and magnetic resonance imaging (MRI) electronics 30. A MRI probe 32 is suspended at the bottom of the probe to provide excitation to the surrounding geologic formation. The excitation field has a generally cylindrical shape as represented by reference numeral 34. Improved devices which can be used for the probe 32 are described generally in U.S. Pat. Nos. 4,710,713; 4,717,876; 4,717,877; and 4,717,878, which, by this reference, are incorporated herein for all purposes.

The spin-spin pulse-echo measurement of the spin-echo relaxation of the sample, in a homogenous isotropic media, reflects the surface-to-volume characteristics of the pores. In typical rocks encountered in the well-logging environment, the rocks are complex mixtures of minerals which often include a variety of pore sizes. Consequently, the measured spin-echo relaxation in such an environment is a complex phenomenon, a reflection of the variations which exist in terms of pore surface-to-volume ratios and surface-to-fluid interactions.

Figure 2:
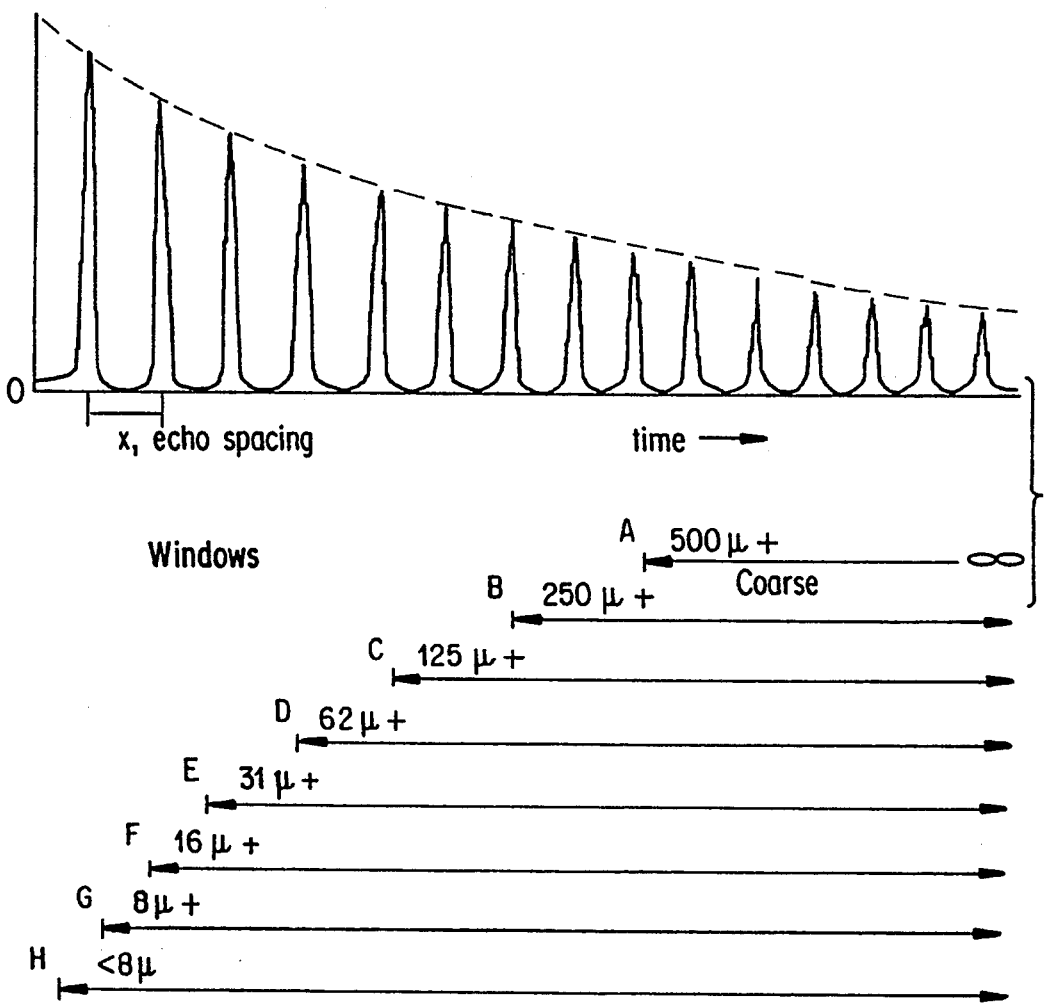
FIG. 2 is a graphical illustration of a chain of spin-echo relaxation signals as a function of amplitude versus time for a geologic structure investigated using a nuclear magnetic resonance system such as that shown in FIG. 1.

FIG. 2 is a graphical illustration of a chain of spin-echo relaxation signals as a function of amplitude versus time for a geologic structure investigated using a nuclear magnetic resonance system such as that shown in FIG. 1. The spacing of the time intervals between the pulses in this application is typically between 1.5 and 3 milliseconds. The time intervals labelled "A–H" correspond to the signal intervals for various particle sizes, with interval "A" corresponding to the interval for particles larger than 500μ and interval "H" corresponding to the interval for particles of larger than 8μ, etc.

Using the echoes in each time window to regress to time zero establishes an apparent porosity amplitude. Such regression techniques are known to those skilled in the art and are described in the following references: K. Fukunaga, *Introduction to Statistical Pattern Recognition*, Academic Press, 1972; Bhattacharyya & Johnson, *Statistical Concepts and Methods*, Wiley & Sons, 1977; and Devijver & Kittler, *Pattern Recognition—A Statistical Approach*, Prentice Hall, 1982.

As a consequence of the actual tool operation, the measurement of spin-echo information is delayed for a few milli-seconds (typically <5 m secs for the tools described in the above referenced patents incorporated herein by reference). During this period of time ($t_{del}$) no formation information is uniquely measured. This $t_{del}$ time period includes the surface-to-volume response associated with a select pore-size group that is directly linked with the pore-sizes related to clay size grains. Thus, by proper selection of the echo windows through use of the $t_{del}$ parameter, a spin-echo measurement can be provided which measures the total pore-space minus those associated with the particular pore surface-to-volume ratios related to the noted particle sizes.

The pore surface-to-volume responses that are missed during this $t_{del}$ period include the clay mineral fraction of the rock-space, thus providing a direct link between such a NMR measured porosity and the total porosity of the rock. In other words, in a clay mineral free environment, with pores >2μ, the NMR echo extrapolation provides a measure of the total porosity but, in a shaly-sand that contains clay minerals and thus clay size pores, the NMR porosity measurement can be made to be free of the influence of the non-reservoir quality micro-pores making the NMR measurement particularly useful in assessing the reservoir's capacity to support production.

Prior art references discussed above (see, for example, A. Timur, *Journal of Petroleum Technology* article) show that NMR may be used for the determination of a rock parameter called the free-fluid index (FFI). The FFI method relies on use of relaxations which occur during a late measurement time following a select $t_{del}$. This time period being referred to as the long component of the relaxation phenomenon (typically $t_{del}$'s ≥ 22 m secs). The difference between the pore space described as the long component relaxation and that provided by the full NMR spectrum provides a direct measure of the pore bulk-volume that is held in place by existing surface tension and other capillary forces. This parameter, the bulk-volume of irreducible water, is directly related to pore surface-to-volume of the non-clay size rock.

In the above-mentioned U.S. Ser. No. 07/701,516, filed May 16, 1991, the content of which is expressly incorporated herein by reference thereto, the NMR measurement of porosity and bulk-volume irreducible are in turn used to find the intrinsic permeability of the rock, since these measured parameters (porosity and bulk-volume irreducible) reflect the principle component of the rock's producibility, through a model such as that of the Coates' free-fluid perm model.

The method and apparatus of the present invention is based on the discovery that NMR values of porosity and bulk-volume irreducible water can be further used to determine the exponential relationship "w" between the bulk-volume water ($BVW = PHI * S_w$) of the formation and the resistivity ratio $R_w/R_t$ through the equation:

$$(PHI*S_w)^w = R_w/R_t \qquad (1)$$

where:

w is the single exponent used to relate the BVW to $R_w/R_t$;

PHI is the rock's total porosity;

$R_w$ is the resistivity of the formation water; and $R_t$ is the rock's true resistivity.

As discussed above, prior art methods could only solve for an apparent w by assuming a water filled condition ($PHI*S_w = PHI$), since prior art devices could measure porosity but not bulk volume irreducible. This resulted in an overestimation of w in hydrocarbon zones. Advantageously, by knowing NMR bulk volume irreducible water (BVI), a second apparent w can be solved for by assuming a hydrocarbon filled formation ($PHI*S_w = BVI$). Thus, the present invention provides accurate values for w for water filled formation as well as for hydrocarbon filled formations.

The apparent values of w are solved for by making two assumptions: First, the zones of the formation are at irreducible water saturation ($S_w = S_{WIRR}$, BVW=BVI, w=wi), and second, that the zones are water filled ($S_w = 1.0$, BVW=PHI, w=ww). Solving Equation (1) for the apparent w's at these two endpoints yields:

$$wi = log(R_w/R_t)/log(BVI) \qquad (2)$$

$$ww = log(R_w/R_t)/log(PHI) \qquad (3)$$

Therefore, since $R_t$ is determinable via a conventional resistivity log as is known in the art, and since BVI and PHI for a given formation are determinable via the NMR devices as described above, once $R_w$ is known, w can be solved for at its two end points, wi and ww.

For typical high porosity shaly sands of the Gulf Coast of the United States, a Pickett Plot has been found useful by those skilled in the art for determining $R_w$. Once $R_w$ is determined via the Pickett Plot, it should be corrected for the effects of clay. Clay correction is also known by those skilled in the art and can be accomplished by using a multiple clay indicator sorting to determine the appropriate clay bound water fraction.

Figure 3:
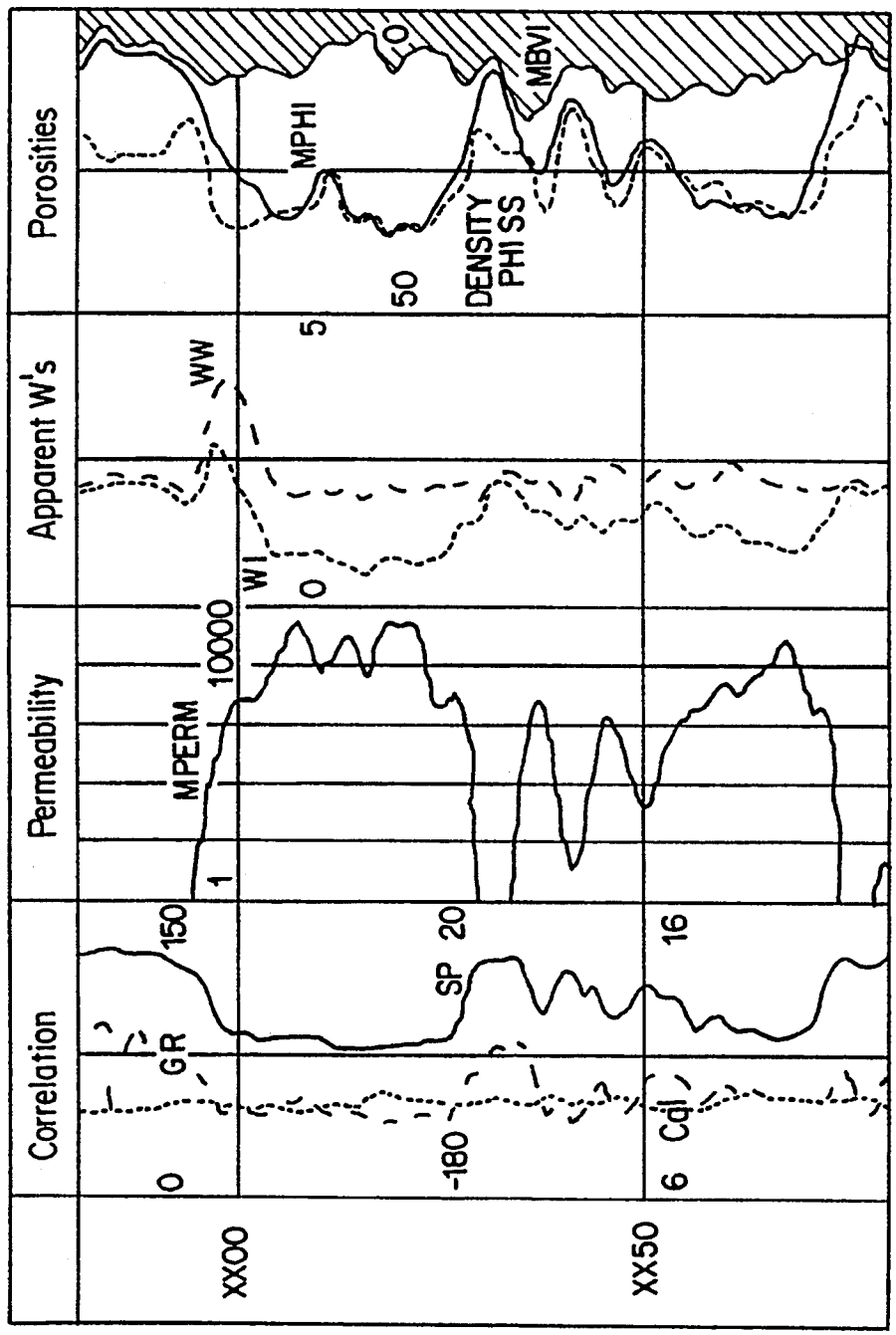
FIG. 3 is a log of typical high porosity sands of the Gulf Coast of the United States and includes the formation's apparent values for w (track 3) and NMR porosity and bulk volume irreducible water (track 4)

Having determined a clay corrected value for $R_w$, the apparent values for w can be ascertained by substituting the NMR measured values for BVI and PHI into Equations (2) and (3), respectively. A log of ww and wi for the above-described Gulf Coast formation can be observed in track 3 of FIG. 3. As expected, when PHI approaches BVI, the two estimates of w tend to approach similar values.

Having determined the apparent values of w, confirmation as to whether these values yield accurate results for the assumed conditions can be ascertained using conventional log interpretation means. Such means will assist in determining whether a particular zone of investigation is likely to be water filled or at irreducible water.

One means for accomplishing this is by plotting ww and wi each separately against a variable strongly linked to saturation, but one that is largely free of formation factor influence, such as the ratio $R_{xo}/R_t$ (where $R_{xo}$ is the flushed zone resistivity). Examples of such plots for ww and wi derived from the above-mentioned high porosity shaly sands of the Gulf Coast of the United States are shown in FIGS. 4 and 5, respectively.

Figure 4:
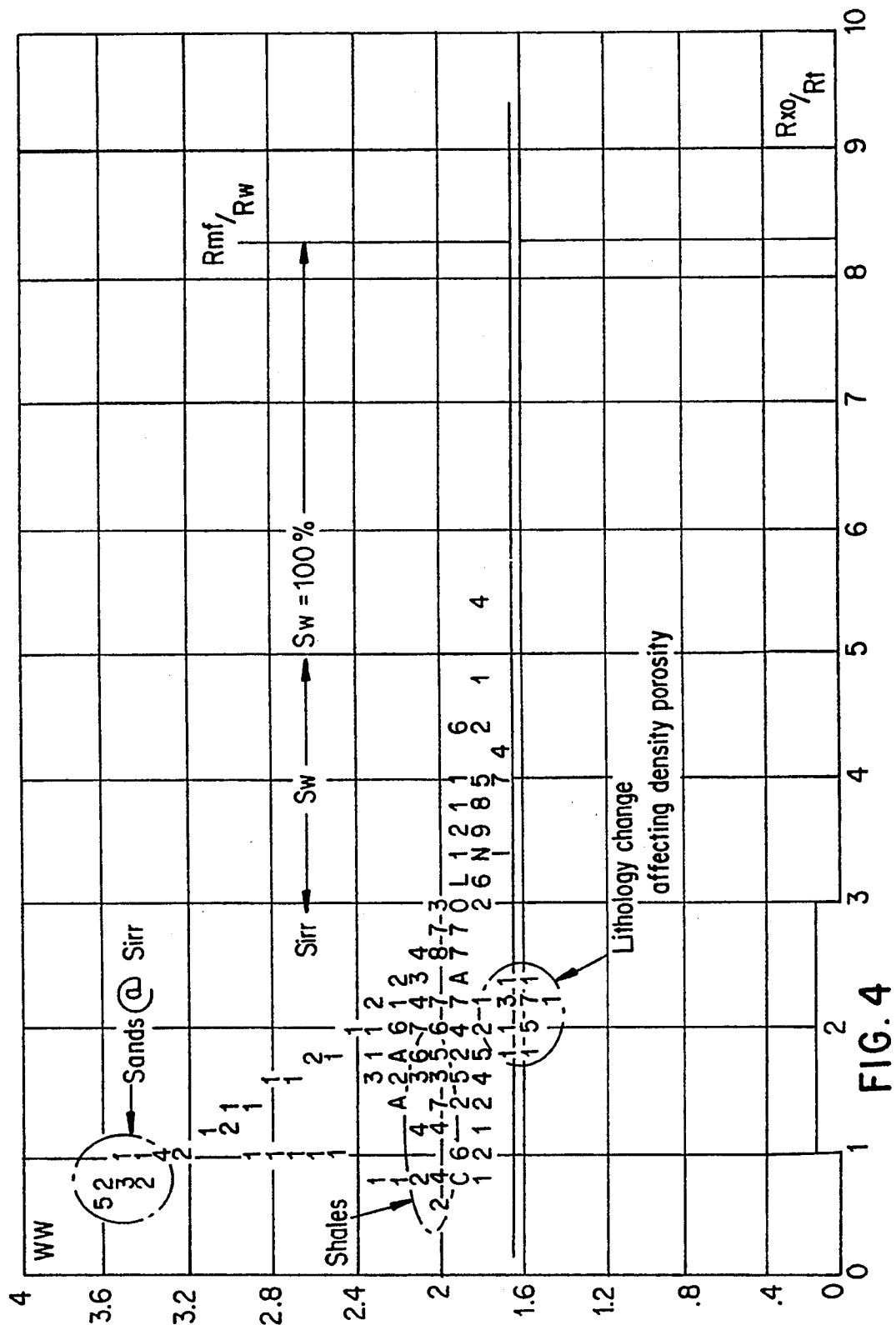
FIG. 4 is a comparison of ww and $R_{xo}/R_t$ for the formation of FIG. 3.

With respect to FIG. 4, several textural conditions should be identifiable to a skilled log analyst and include: sands at irreducible, sands approaching $S_w=1$, shaly sections, a mineral change and trends reflecting the effects of clay minerals and hydrocarbon content. Of particular importance, in water sands, at or near the assumed condition, i.e., $S_w=1$, ww approaches a value of 1.8. This value corresponds well to values often observed in lab studies of similar rocks. Thus, ww provides an accurate determination of w as we approach the assumed condition of PHI*$S_w$=PHI.

Figure 5:
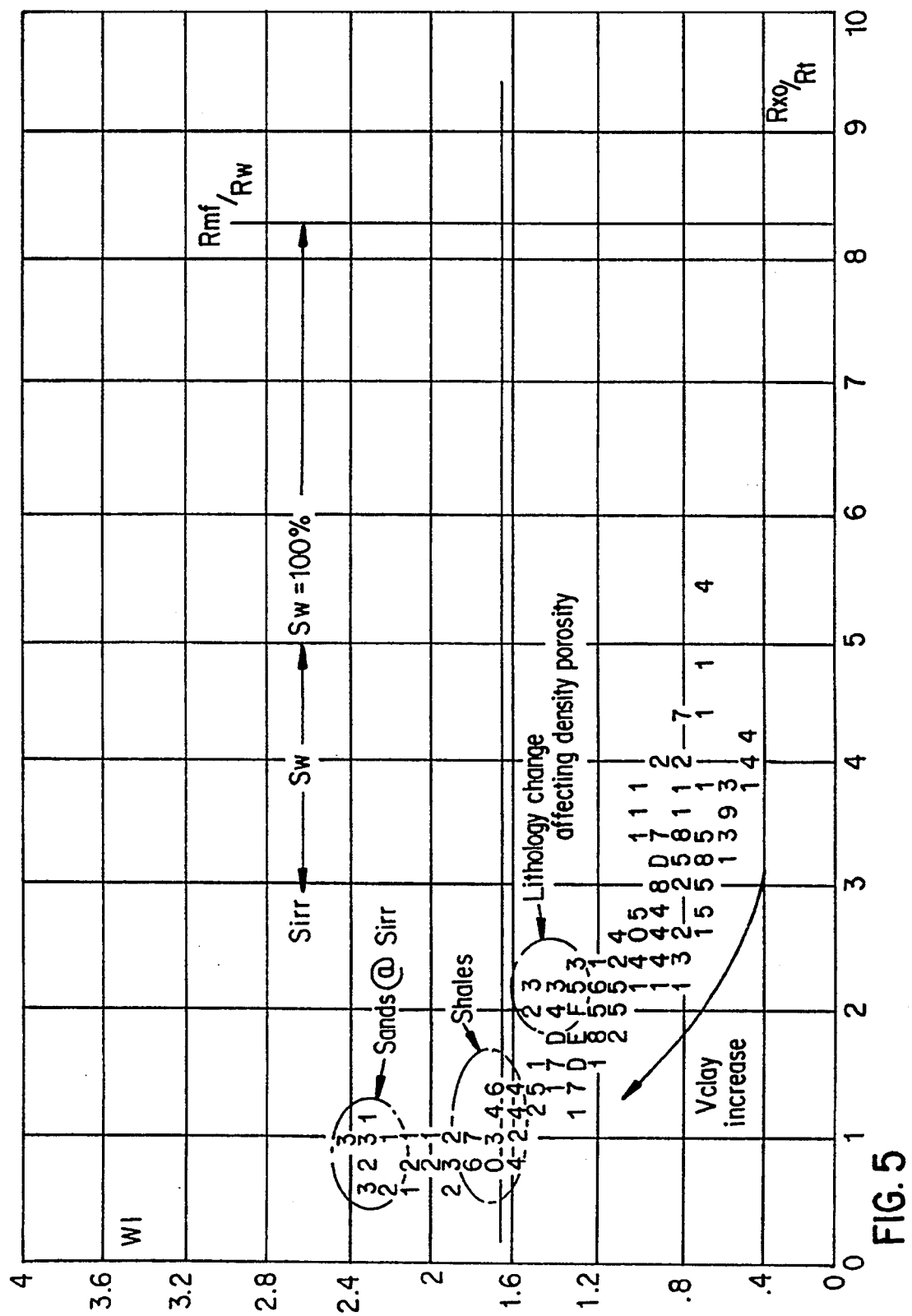
FIG. 5 is a comparison of wi and $R_{xo}/R_t$ for the formation of FIG. 3.

With respect to FIG. 5, the wi plot illustrates the changes in data patterns associated with the change in assumption. Now the sands that are high in hydrocarbon content give values more in line with values observed in laboratory studies for similar rock, while the non-irreducible areas give values much lower. Thus, wi provides an accurate determination of w as we approach the assumed condition of PHI*$S_w$=BVI.

Furthermore, of particular importance is the observation from FIGS. 4 and 5 that w apparently varies with irreducible water saturation. As shown in FIG. 5, as wi decreases, $S_w$ increases. This means the prior art use of constant values for "m" and "n" in both water and hydrocarbon zones may lead to error, since it results in over estimating hydrocarbon content in some formations while underestimating them in others.

Figure 6:
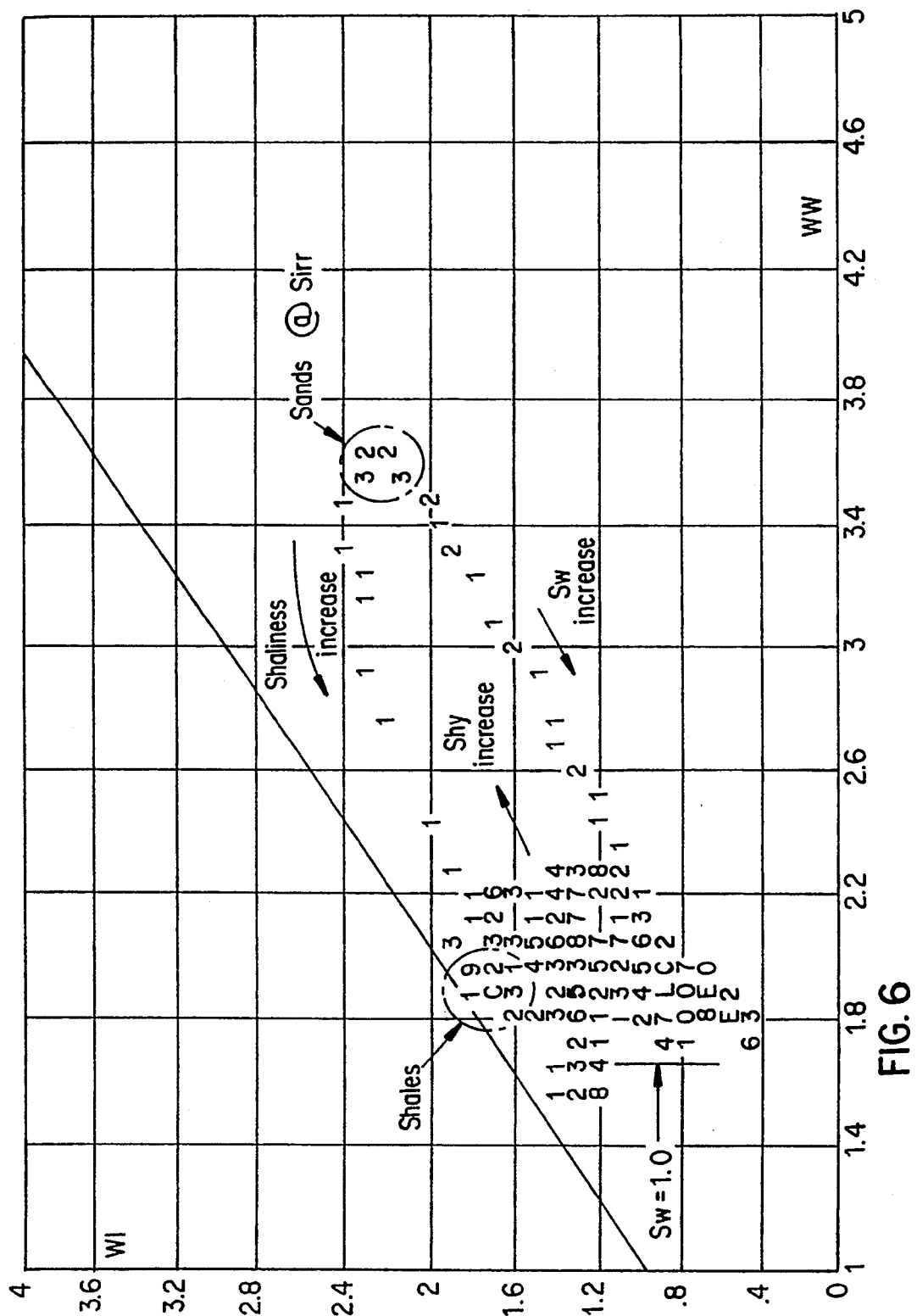
FIG. 6 is a comparison of ww and wi for the formation of FIG. 3.

This trend is further explored in FIG. 6, a plot of wi against ww. Examining FIG. 6, it can be observed by one skilled in that art that water bearing sands are a vertical trend at a value near 1.8, while the sands at $S_{WIRR}$ trend to the right and above this same value.

Figure 7:
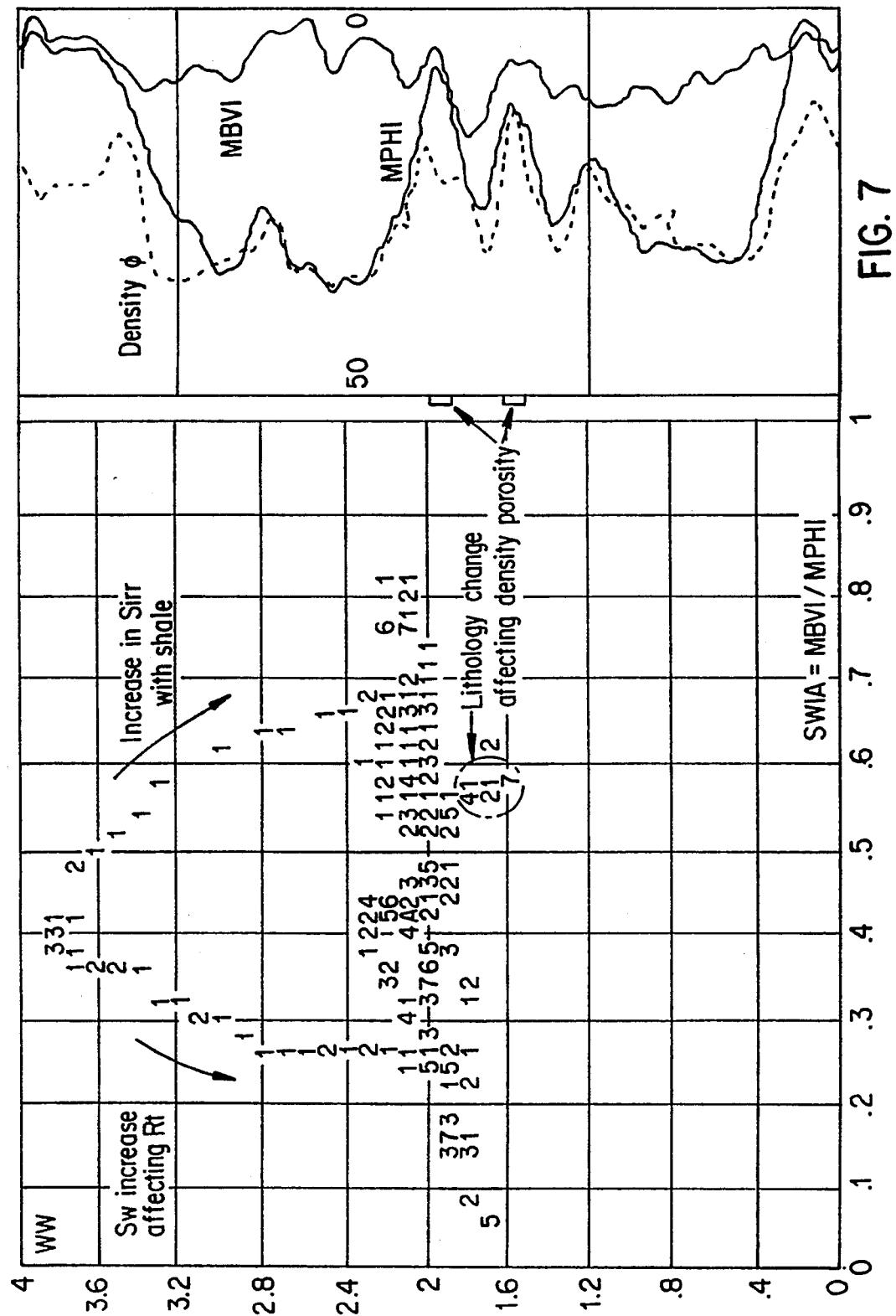
FIG. 7 is a comparison of ww and S$_{WIRR}$ (determined from NMR measurements of bulk-volume irreducible water and porosity) for the formation of FIG. 3.

Further confirmation of w's variation with irreducible water saturation is ascertained from FIG. 7, a plot of ww against the apparent $S_{WIRR}$, where the apparent $S_{WIRR}$ is equivalent to the NMR measured bulk volume irreducible water BVI divided by the NMR measured porosity PHI. FIG. 7 makes it possible to discern trends associated with the effects of increasing $S_w$ as well as trends of increasing $S_{WIRR}$. Importantly, a trend between $S_{WIRR}$ and w is also shown, providing a pattern to develop a relationship for predicting the value of w to use in a shaly sand formation like these. Determining the best-fit first order equation from the trend depicted in FIG. 7 results in the following equation:

$$w = 0.4 * S_{WIRR} + 1.65 \quad (4)$$

Figure 8:
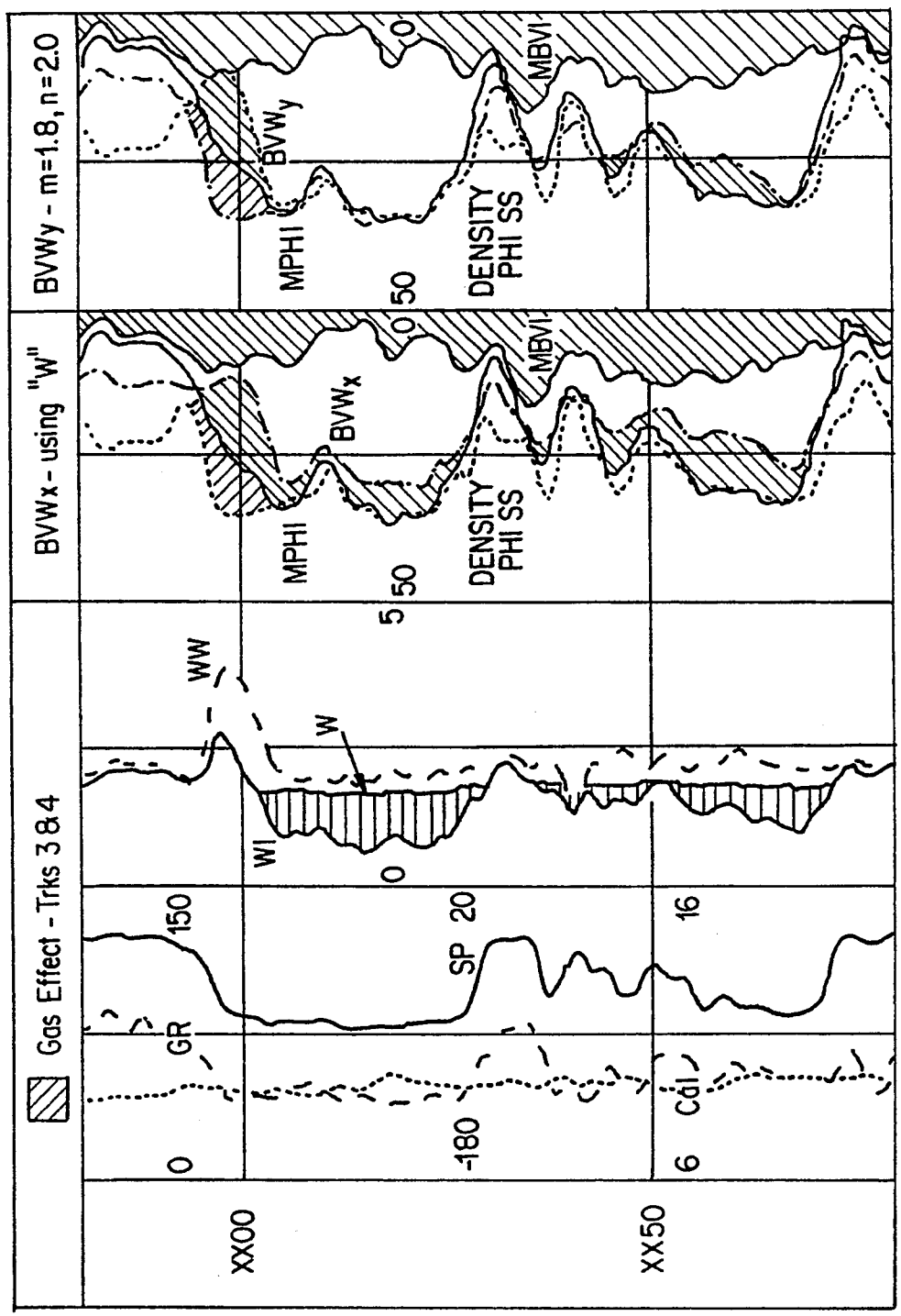
FIG. 8 is a comparison of conventional results (track 4) to those obtained by the method of the present invention (track 3) in determining bulk volume water for the formation of FIG. 3.

Track 2 of FIG. 8 shows a log of w (calculated using equation (4)), wi and ww for the above-described formation. The resulting bulk-volume water calculated using w, where the w to be used is constrained to be greater than or equal to wi and less than or equal to ww since ww and wi represent the endpoints of w, is shown in track 3 of FIG. 8. As can be observed, compared to the conventional "m" and "n" analysis depicted in track 4, the results have increased the water in some of the original "shows" while reducing it in others.

FIG. 8 also illustrates the capability of the w information to predict $S_{WIRR}$ qualities by comparing the predicted w to ww and wi. As can be observed, when ww>w hydrocarbons are present, and when w is greater than wi, a non-$S_{WIRR}$ zone is indicated. Only when w=wi, can the zone be considered at $S_{WIRR}$.

For the above-described formation, the show at the top of the upper sand of FIG. 8 was production tested, making 600 mcfpd of gas for 30 days then producing about 20 BWPD and 50 BOPD, finally leveling off at 100 BWPD and 40 BOPD.

EXAMPLE

Figure 9:
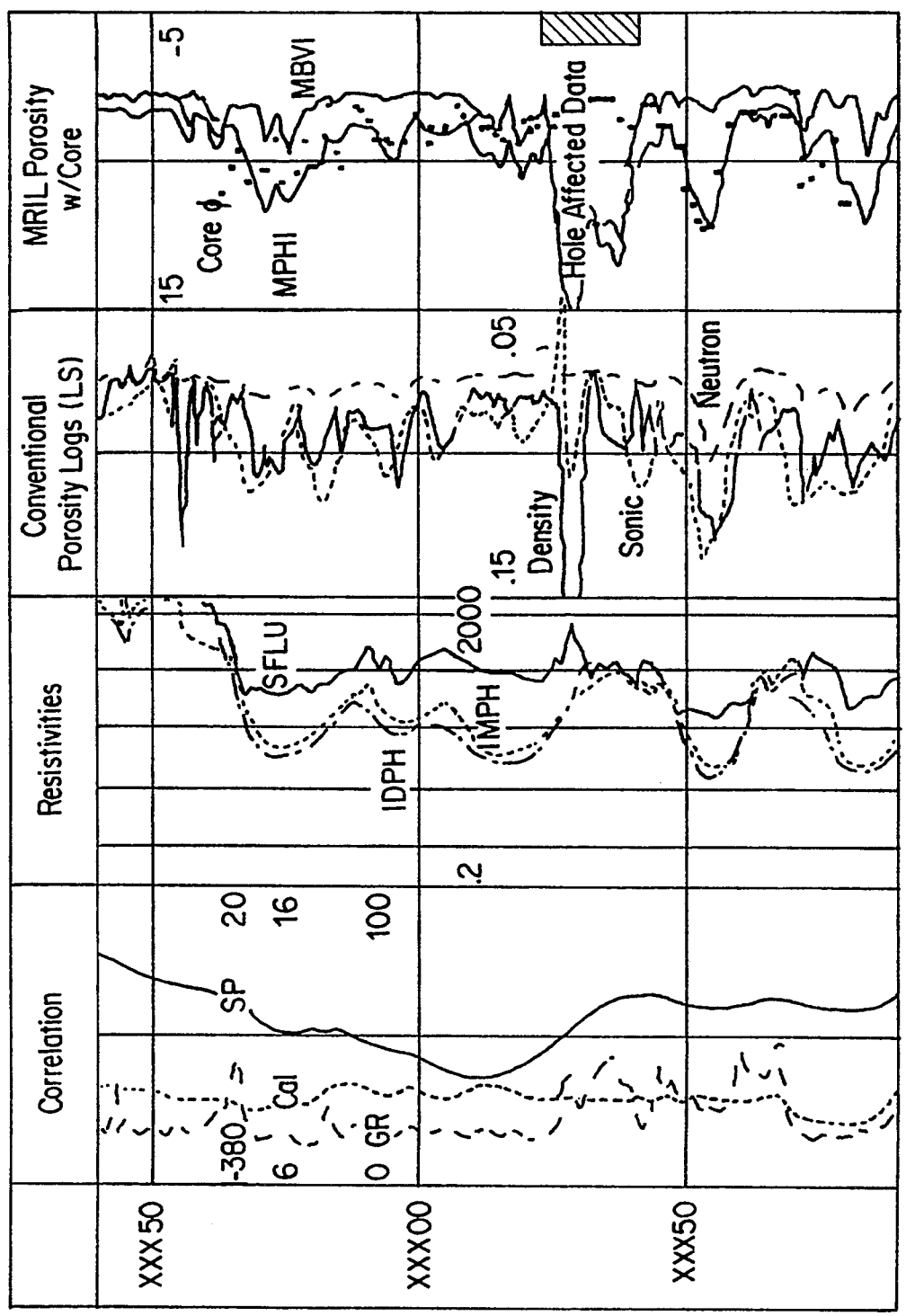
FIG. 9 is a log of a carbonate Edward's formation.

A carbonate formation more complex than the above-described shaly sand formation was investigated to verify the above-described results. FIG. 9 illustrates the log data for this formation. The interval shown is an Edward's formation from central Texas. As shown by the conventional porosity logs, (track 3 of FIG. 9) displayed in apparent limestone porosity units, the lithology is complex, and establishing the correct values for "a", "m", and "n" is difficult. However, the NMR derived porosity closely tracks the core derived porosity (track 4 of FIG. 9), demonstrating the NMR log's capability to determine porosity without concern for matrix lithology. Thus, the problem of determining porosity for a complex lithology is minimized, leaving the issue of relating porosity to formation factor.

Figure 10:
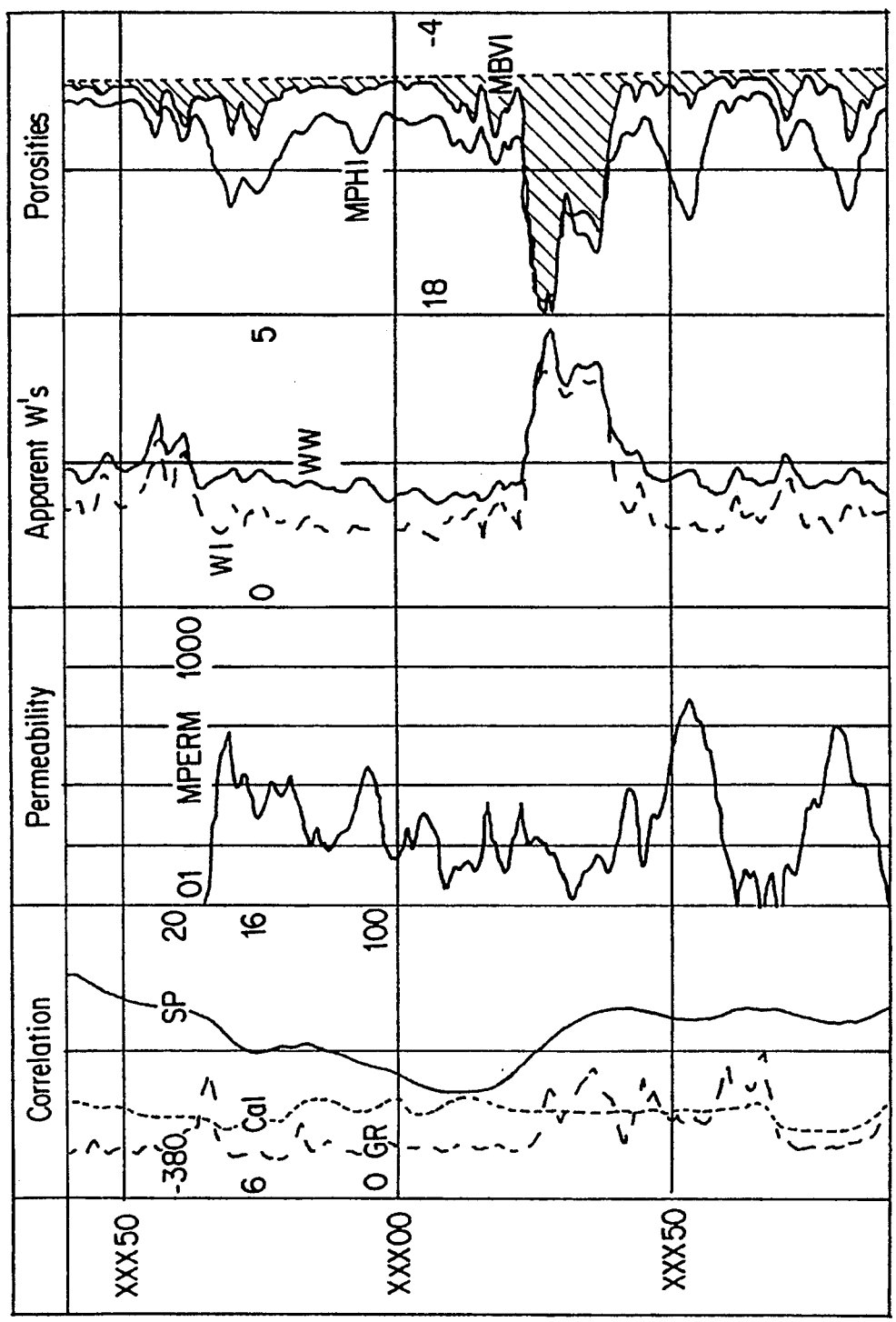
FIG. 10 is a comparison of the values of ww and wi for the formation of FIG. 9.
Figure 11:
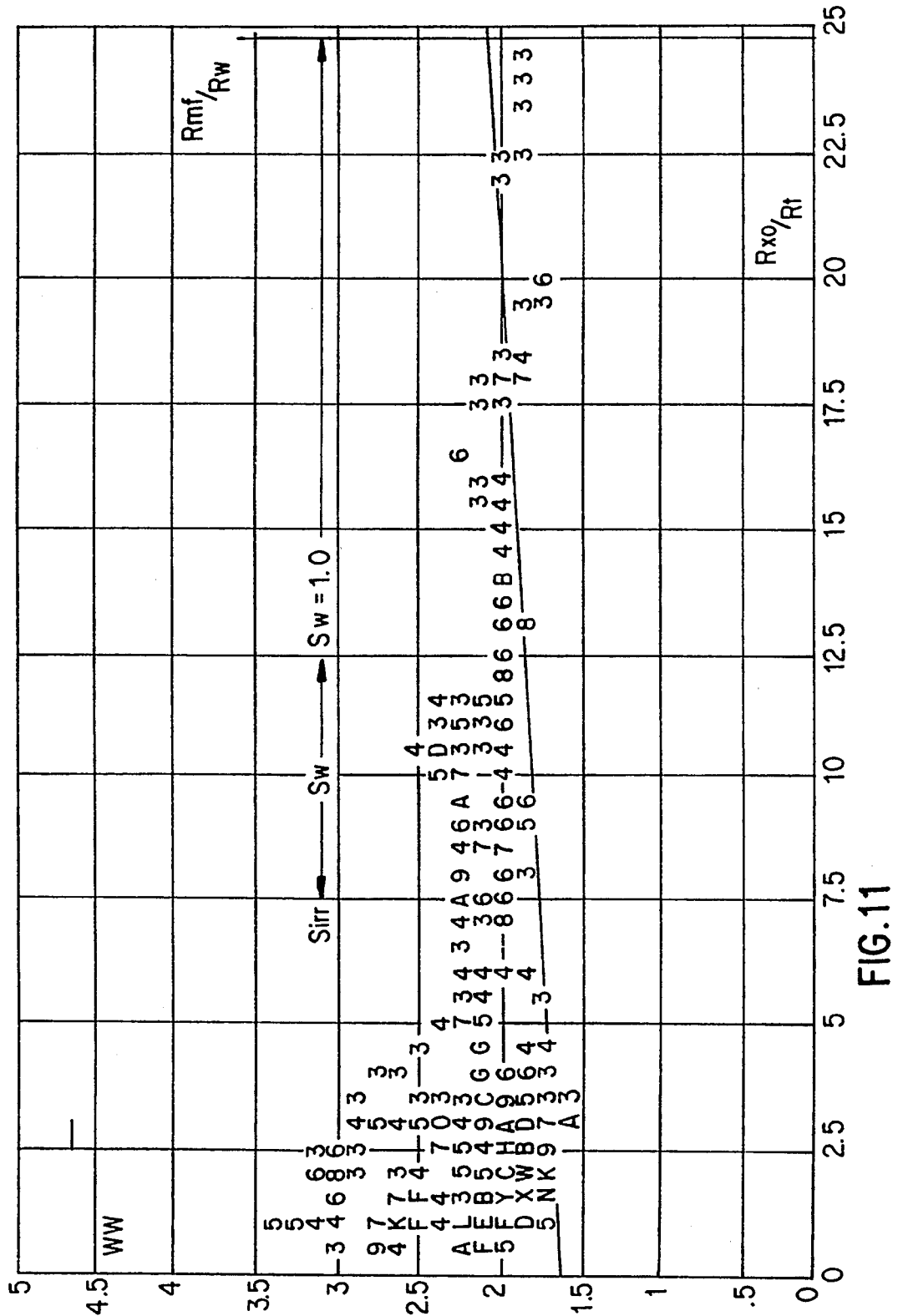
FIG. 11 is a comparison of ww and $R_{xo}/R_t$ for the formation of FIG. 9.
Figure 12:
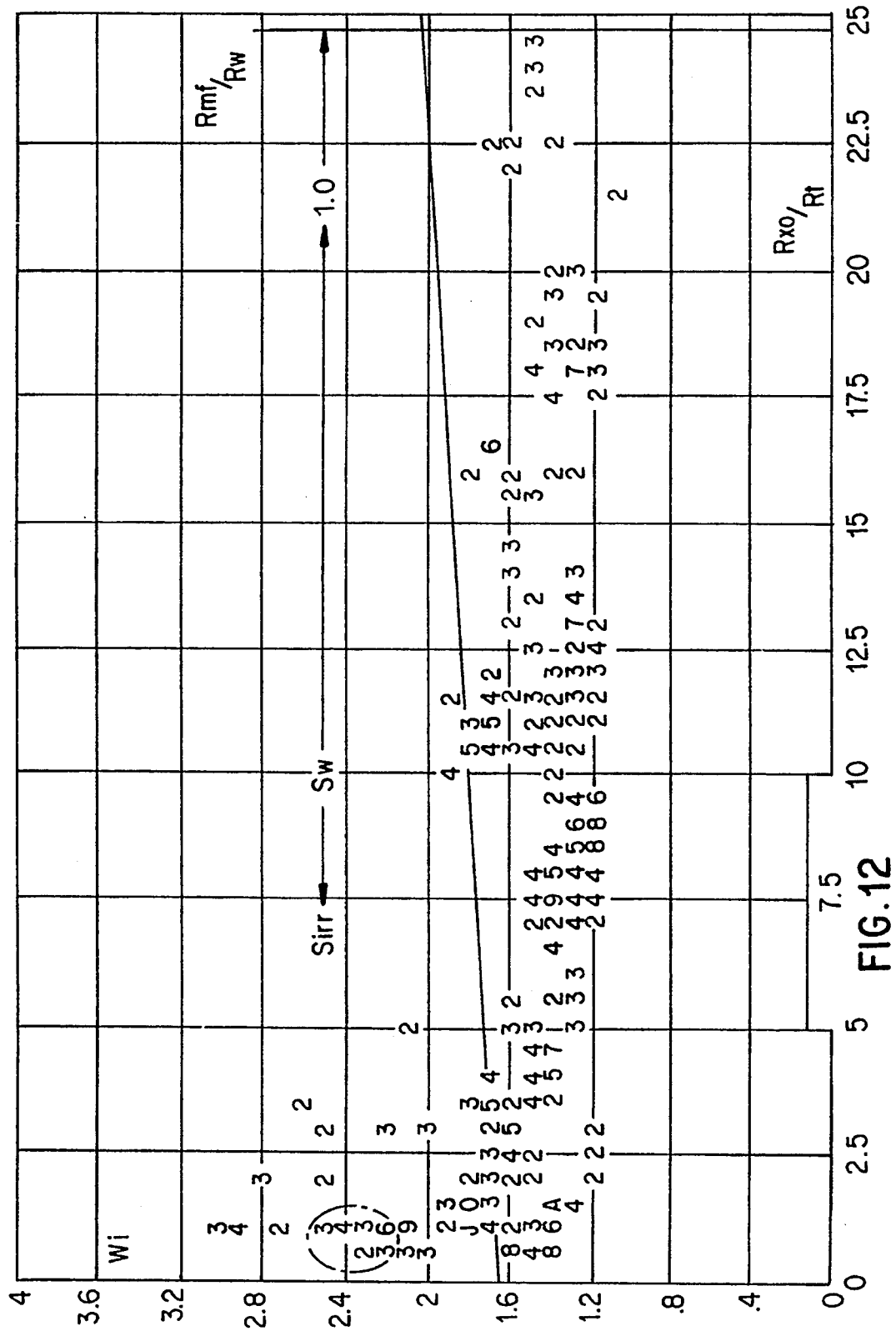
FIG. 12 is a comparison of wi and $R_{xo}/R_t$ for the formation of FIG. 9.
Figure 13:
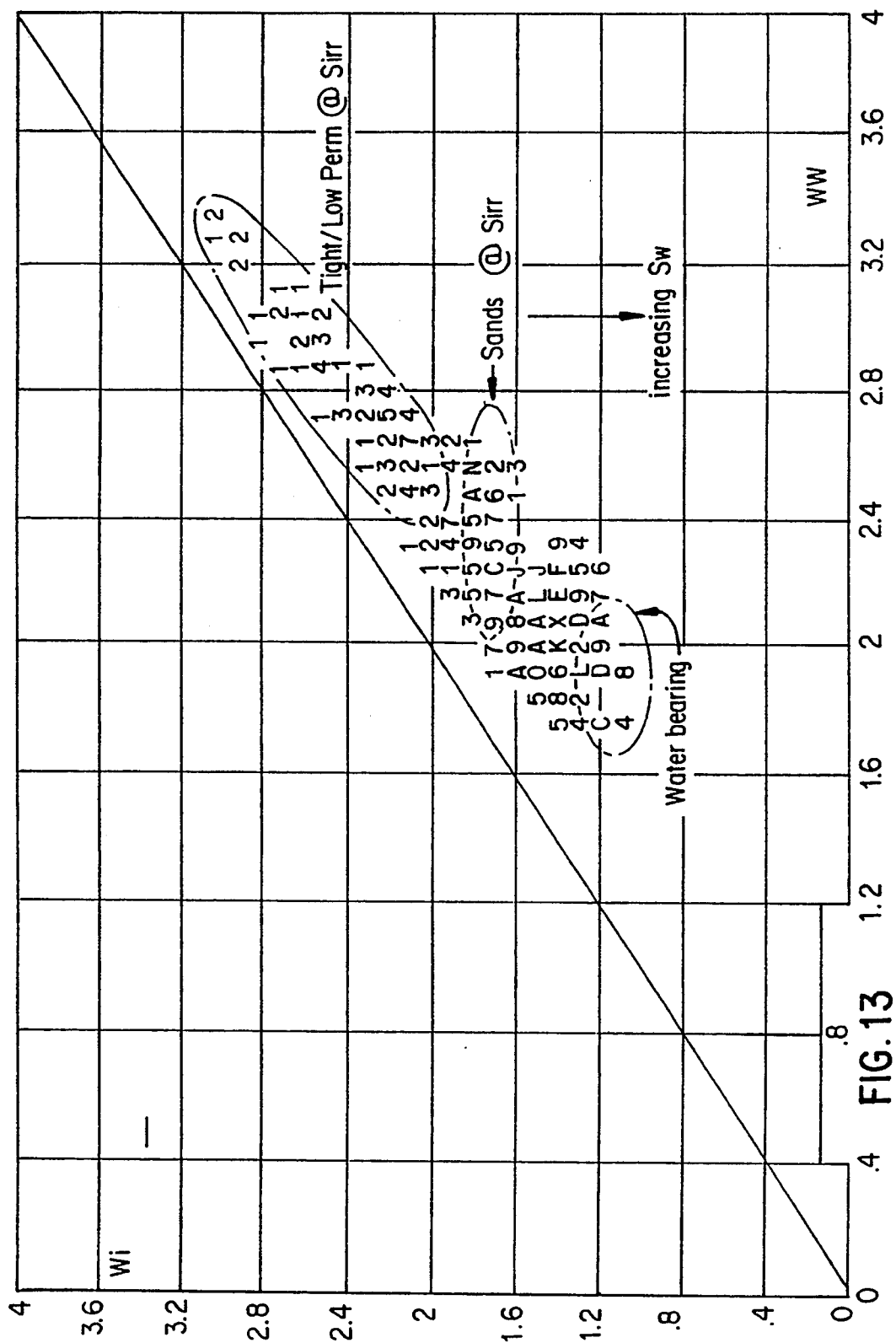
FIG. 13 is a comparison of wi and ww for the formation of FIG. 9.

The first pass analog results of wi and ww are shown in track 3 of FIG. 10. The ww versus $R_{xo}/R_t$ plot of this interval is shown in FIG. 11. The high $R_{xo}/R_t$ maximum gives good confirmation that a major portion of this interval has a high water content. Looking next at the BVI based wi versus $R_{xo}/R_t$ plot, FIG. 12, confirms the high water content and evidences that there are hydrocarbons present. This is indicated by the contrast in ww and wi in FIGS. 11 and 12. These conclusions are also supported by the trends observable in FIG. 13, a plot of wi against ww.

Figure 14:
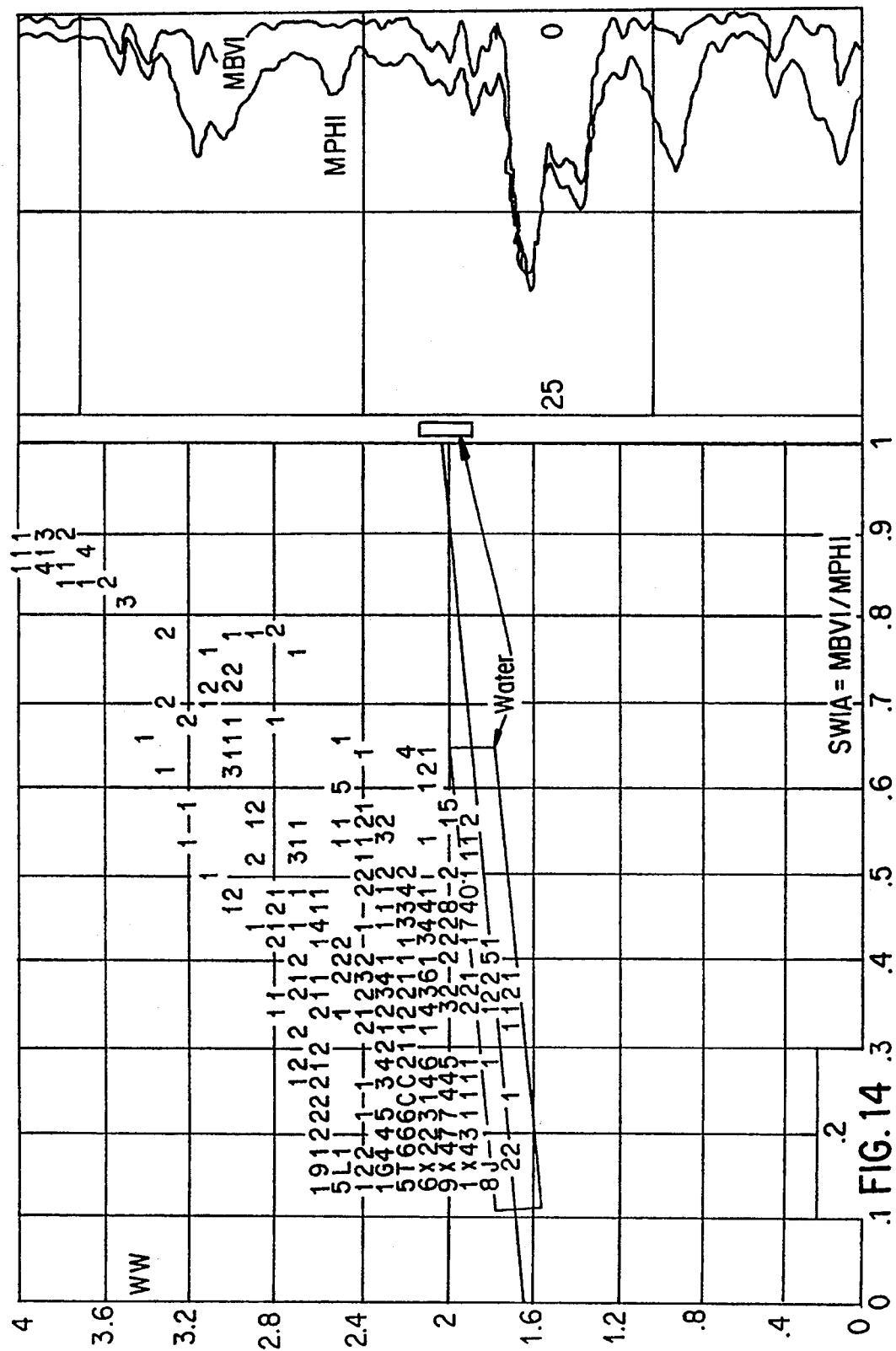
FIG. 14 is a comparison of ww and S$_{WIRR}$ (determined from the NMR measurementS of bulk-volume irreducible water and porosity) for the formation of FIG. 9.

A comparison of ww to $S_{WIRR}$ is shown in FIG. 14, where $S_{WIRR}$ is derived from the NMR values of porosity and bulk volume irreducible as described above. The trend observed in the above-discussed Gulf-Coast shaly sand example in shown as a solid line (equivalent to Equation (4)). As can be observed, the solid line closely agrees with the lower edge of the data confirming the viability of Equation (4) to this type of formation. The data that falls above this line infers non-reservoir rock (shales) at $S_{WIRR}$ or hydrocarbon effects.

Table 1 shows the results of full core analysis on similar rocks from a nearby well in this field. The results of transforming the conventional a, m, and n values into w are also listed.

TABLE 1

| Depth | m | n | w | PHI | PERM | SAT |
|---|---|---|---|---|---|---|
| 10380.80 | 1.888 | 1.230 | 1.802 | 12.800 | 1.200 | 73.500 |
| 10382.60 | 2.063 | 1.020 | 1.738 | 6.300 | .510 | 28.600 |
| 10383.60 | 2.021 | 1.020 | 1.823 | 6.700 | .130 | 51.300 |
| 10451.40 | 2.119 | 1.120 | 1.796 | 9.200 | .910 | 32.00 |
| 10452.80 | 2.111 | 1.230 | 1.758 | 9.700 | 2.500 | 21.00 |
| 10453.40 | 2.055 | 1.160 | 1.688 | 11.200 | 5.500 | 21.900 |

Figure 15:
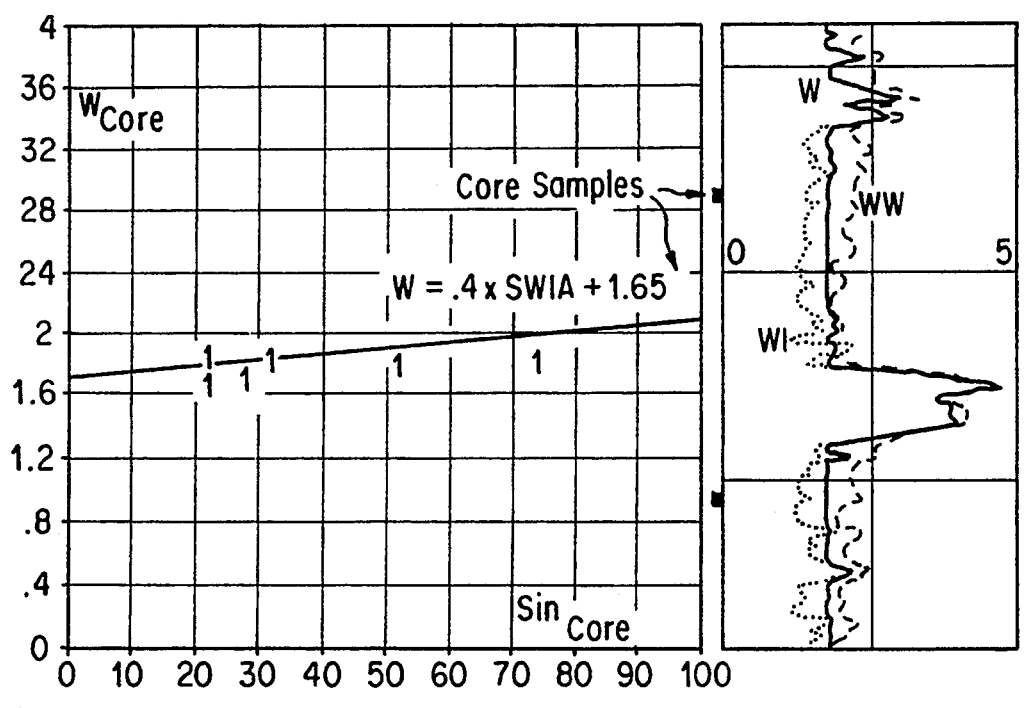
FIG. 15 is a comparison of core determined S$_{WIRR}$ and w for core samples taken from a well near the formation of FIG. 9.

FIG. 15 shows a plot of the derived w from Table 1 against core $S_{WIRR}$. Additionally, FIG. 15 also contains a solid line representing the trends observed on both the shaly sand and the log derived values shown in FIG. 14 (i.e., Equation 4). Though the data set is limited, it gives a fairly reasonable agreement to the observed trend.

Figure 16:
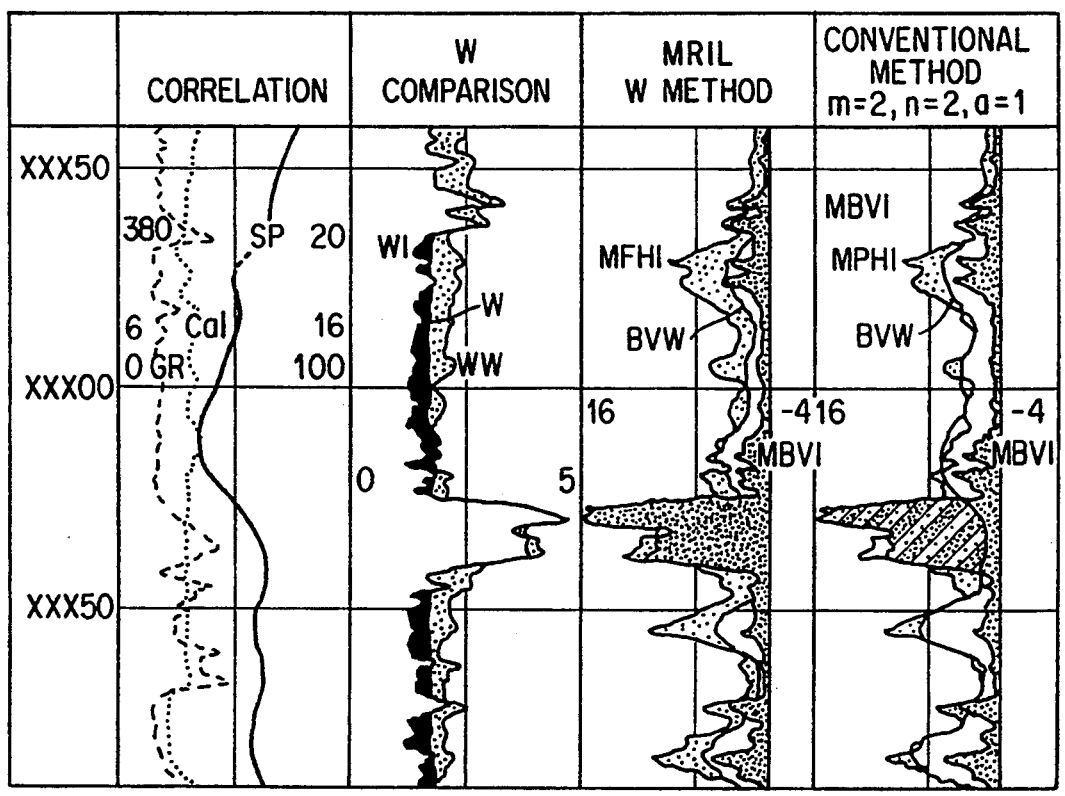
FIG. 16 is a comparison of convention results (track 4) to those obtained by the method of the present invention (track 3) in determining bulk-volume water for the formation of FIG. 9.

The actual w (as well as the apparent w's) calculated via equation (4) is shown in track 2 of FIG. 16. To determine the BVW term, the w to be used is first calculated via equation (4) and then constrained to be greater than or equal to wi and less than or equal to ww as discussed above. The results (track 3) show that most of the good permeability section is in a non-$S_{WIRR}$ state.

The production tests on this well confirmed this by initially producing a 1.1 MMCF gas with low water flow from all major porosities in this interval. However, that quickly changed to non-commercial high water cut production in less than 60 days.

Although the present invention has been described in connection with the preferred embodiment, it is not intended to be limited to the specific form set forth herein, but on the contrary, it is intended to cover such modifications, alternatives, and equivalents as can be reasonably included within the spirit and scope of the invention as defined by the appended claims.

I claim:

1. A method for determining the composition of a geologic structure using a NMR logging tool, comprising the steps of:

imparting a polarizing magnetic field to a geologic structure for a predetermined period of time;

measuring nuclear magnetic resonance signals representing spin-echo relaxation of a population of particles in the geologic structure;

constructing a chain of spin-echo signals characteristic of said population of particles;

determining values for the porosity (PHI) of the geologic structure from said chain of spin-echo signals;

determining values for the bulk-volume irreducible water (BVI) of the geologic structure from said chain of spin-echo signals; and deriving additional petrophysical properties of the geological structure from said porosity (PHI) values and from said bulk volume irreducible water (BVI) values and displaying the derived properties in a human-readable form.

2. The method according to claim 1 wherein an additional petrophysical property of the geologic structure is the bulk-volume water (BVW) of the geologic structure.

3. The method according to claim 2 further comprising the steps of:

determining an $R_w/R_t$ ratio of the geologic structure, where $R_w$ is the resistivity of the formation water and $R_t$ is the true formation resistivity;

relating the BVW value of the geologic structure to the $R_w/R_t$ ratio of the geologic structure through an expression having a single exponent w;

determining values for said single exponent w from said PHI values and from said BVI values; and using said determined values for said single exponent w to solve said expression for the BVW values of the geologic structure.

4. The method according to claim 3 wherein said single exponent expression is:

$$BVW^w = R_w/R_t.$$

5. The method according to claim 4 wherein the step of determining values for said single exponent includes:

using said PHI values to determine a set of first apparent values ww of said single exponent w for the geologic structure by assuming the geologic structure is water filled, thereby reducing said single exponent expression to:

$$ww = \log(Rw/Rt)/\log(PHI);$$

using said BVI values to determine a set of second apparent values wi of said single exponent w for the geologic structure by assuming said geologic structure is at irreducible water saturation, thereby reducing said single exponent expression to:

$$wi = \log(Rw/Rt)/\log(BVI);\ \text{and}$$

interpreting said first and said second apparent values to determine the values of said single exponent w for the geologic structure.

6. The method according to claim 5 wherein the step of interpreting includes:

comparing said first apparent values ww to the ratio $R_{xo}/R_t$ of the geologic structure, where $R_{xo}$ is the flushed zone resistivity;

comparing said second apparent values wi to the ratio $R_{xo}/R_t$ of the geologic structure;

estimating the water saturation condition $S_w$ value of the geologic structure based on said comparisons; and selecting a value for said single exponent w from said first and second apparent values based on the $S_w$ value.

7. The method according to claim 5 wherein said first apparent values are determined by assuming that the $S_w$ value is approximately 1.

8. The method according to claim 5 wherein said second apparent values are determined by assuming that the $S_w$ value is approximately equal to an irreducible water saturation ($S_{WIRR}$) value of the geologic formation.

9. The method according to claim 6 further comprising the step of:

determining textural changes of the geologic structure from said comparisons.

10. The method according to claim 6 further comprising the steps of:

comparing said first and said second apparent values to the ratio $R_{xo}/R_t$ of the geologic structure to determine whether said single exponent w varies with the $S_{WIRR}$ value of the geologic structure; and comparing said first apparent values ww to said second apparent values wi to determine whether said single exponent w varies with the $S_{WIRR}$ value of the geologic structure.

11. The method according to claim 6 further comprising the steps of:

comparing said first apparent values ww to the $S_{WIRR}$ value of the geologic structure; and deriving a second expression relating said single exponent w to the $S_{WIRR}$ value of the geologic structure from said comparison of said first apparent values ww to the $S_{WIRR}$ value of the geologic structure.

12. The method according to claim 11 wherein the $S_{WIRR}$ value is equal to said BVI water divided by said porosity PHI.

13. The method according to claim 11 wherein said step of deriving said second expression includes:

determining the best-fit curve from said comparison of said first apparent values ww to the an irreducible water saturation ($S_{WIRR}$) value of the geologic structure.

14. The method according to claim 11 wherein said second expression is:

$$w = 0.4 * S_{WIRR} + 1.65.$$

15. The method according to claim 14 wherein the $S_{WIRR}$ value is equal to said bulk-volume irreducible water BVI divided by said porosity PHI.

16. The method according to claim 15 further comprising the steps of:
using said values for BVI and PHI to solve said second expression for values of w for the geologic structure; and
using said values of w to determine the bulk volume water of the geologic structure by solving said single exponent expression for the bulk volume water of the geologic structure.

17. The method according to claim 16 wherein w is constrained to greater than or equal to wi and less than or equal to ww.

18. The method according to claim 16 further comprising the step of determining the presence of hydrocarbons by:
comparing the values of said single exponent w determined for the geologic structure via said second expression to said first apparent values ww, hydrocarbons being present when ww>w.

19. The method according to claim 16 further comprising the step of determining a non-irreducible water saturation condition by:
comparing the values of said single exponent w determined for the geologic formation via said second expression to said second apparent value wi, a non-irreducible water saturation condition being present when w>wi.

20. The method according to claim 16 further comprising the step of determining an irreducible water saturation condition by:
comparing the values of said single exponent w determined for the geologic formation via said second expression to said second apparent value wi, an irreducible water saturation condition being present when w=wi.

* * * * *